(12) United States Patent
Kim

(10) Patent No.: US 8,398,669 B2
(45) Date of Patent: Mar. 19, 2013

(54) INDWELLING FECAL DIVERTING DEVICE

(75) Inventor: Jae-Hwang Kim, Daegu (KR)

(73) Assignees: Jae-Hwang Kim, Daegu (KR); Yushin Medical Co., Ltd., Bucheon (KR)

( * ) Notice: Subject to any disclaimer, the term of this patent is extended or adjusted under 35 U.S.C. 154(b) by 1944 days.

(21) Appl. No.: 10/491,245

(22) PCT Filed: Apr. 9, 2002

(86) PCT No.: PCT/KR02/00614
§ 371 (c)(1),
(2), (4) Date: Jul. 7, 2004

(87) PCT Pub. No.: WO03/086507
PCT Pub. Date: Oct. 23, 2003

(65) Prior Publication Data
US 2005/0033226 A1    Feb. 10, 2005

(51) Int. Cl.
*A61M 29/00* (2006.01)
(52) U.S. Cl. .................................. 606/197; 604/101.01
(58) Field of Classification Search .............. 604/96.01, 604/101.01; 606/197
See application file for complete search history.

(56) References Cited

U.S. PATENT DOCUMENTS

| | | | | |
|---|---|---|---|---|
| 3,789,847 A | * | 2/1974 | Lehmann | ................. 606/197 |
| 3,828,782 A | * | 8/1974 | Polin | .................. 604/103.03 |
| 4,676,778 A | | 6/1987 | Nelson, Jr. | |
| 5,312,343 A | * | 5/1994 | Krog et al. | ............... 604/101.03 |
| 5,443,445 A | * | 8/1995 | Peters et al. | ................... 604/27 |
| 5,569,216 A | * | 10/1996 | Kim | ............................. 604/277 |
| 6,045,531 A | * | 4/2000 | Davis | ....................... 604/101.05 |
| 6,527,755 B1 | * | 3/2003 | Salama | ......................... 604/348 |
| 6,926,689 B2 | * | 8/2005 | Scheule | ...................... 604/6.16 |

FOREIGN PATENT DOCUMENTS

| GB | 2 243 553 A | 11/1991 |
|---|---|---|
| GB | 2243553 A * | 11/1991 |

* cited by examiner

*Primary Examiner* — Jason Flick
(74) *Attorney, Agent, or Firm* — Birch, Stewart, Kolasch & Birch, LLP

(57) ABSTRACT

Disclosed is an indwelling fecal diverting device. The device comprises an elongate tube formed, at an upper end thereof, with a tubular body part; a pair of fixing balloons attached up and down to an outer surface of the tubular body part such that a clamping portion is defined between the fixing balloons; and a tube opening and closing balloon attached to an inner surface of the tubular body part. An injection passage is defined in the tube so that a remedial liquid can be injected through the injection passage to the outside of the tube to medically treat an anastomosed portion of an intestinal tract of a patient. The indwelling fecal diverting device is fitted into the intestinal tract of the patient, air is supplied into the fixing balloons to inflate them, and the intestinal tract is clamped around the clamping portion using a clamping band.

13 Claims, 6 Drawing Sheets

INDWELLING FECAL DIVERTING DEVICE

TECHNICAL FIELD

The present invention relates to an indwelling fecal diverting device for a patient having undergone an operation on a part of his or her intestinal tract such as a rectum, a large intestine, and so forth, and more particularly, the present invention relates to an indwelling fecal diverting device which is disposed upward of an anastomosed portion of an intestinal tract when there is concern about leakage of liquid and gas at the anastomosed portion of a rectum or large intestine after a patient has undergone an operation on the rectum or large intestine, so that feces can be discharged without coming into contact with the anastomosed portion, thereby effectively protecting the anastomosed portion, ensuring superior safety and easy installation thereof, and permitting use thereof for a desired period of time.

BACKGROUND ART

Generally, when there is danger of leakage of liquid and gas at an anastomosed portion of a rectum or large intestine after a patient has undergone an operation on the rectum or large intestine, in order to divert indwelling feces with an aim of preventing the leakage, an abdominal colostomy device is used. This abdominal colostomy device has been widely adopted in advanced countries, mainly for aged or feeble persons or a person who has undergone radiotherapy before an operation. Leakage of liquid and gas results in a very dangerous situation, which can also lead to a lawsuit.

In order to avoid permanent installation of the abdominal colostomy device, a temporary abdominal colostomy was disclosed in the art. However, in the case of installing a temporary abdominal colostomy device, it cannot be removed until 2~3 months have elapsed. Also, 30~60% of patients cannot be restored to an original state and therefore lives for the rest of his or her life with the temporary abdominal colostomy device installed. That is to say, while an operation must be performed again for removing the temporary abdominal colostomy device, since an aged or feeble person has a weak health condition, it is dangerous for the patient to undergo the second operation.

To cope with these drawbacks, recently, a fecal discharging device has been disclosed in the art. The fecal discharging device comprises a tube which is made of a thin elastic waterproof material. The tube is sutured to an inner wall of an intestinal tract at a position 5~10 cm upward of an anastomosed portion of the intestinal tract, so that feces can be discharged without coming into contact with the anastomosed portion.

Nevertheless, the fecal discharging device, which is also referred to as a "colon shield", still has disadvantages as described below, and therefore, is not widely used.

It is difficult to suture the vinyl tube to the inner wall of the intestinal tract, and an extended period of time is required. In particular, the chance that the thin tube will be held properly sutured to the inner wall of the intestinal tract is so slim that stability is doubted upon use of the colon shield.

While the thin tube constituting the fecal discharging device can be easily removed due to the fact that it is naturally detached from the inner wall of the intestinal tract within about 5~10 days, a defect is caused in that it is difficult to effect indwelling fecal diversion through a desired period of time.

DISCLOSURE OF THE INVENTION

Accordingly, the present invention has been made in an effort to solve the problems occurring in the related art, and an object of the present invention is to provide an indwelling fecal diverting device which allows feces of a patient having undergone an operation on a rectum or large intestine to be discharged without coming into contact with an anastomosed portion, thereby ensuring superior safety and easy installation thereof, and permitting use thereof through a desired period of time.

In order to achieve the above object, according to the present invention, a fecal discharging device is constructed and used in a state wherein it is fixed in an intestinal tract of a patient having undergone an operation on a rectum or large intestine.

Concretely speaking, a tube is made of a material which is harmless to the human body and capable of being freely flexed. A tubular body part is formed at an upper end of the tube. A pair of fixing balloons are attached up and down to a circumferential outer surface of the tubular body part in a manner such that a clamping portion is defined between the fixing balloons. A tube opening and closing balloon is attached to a circumferential inner surface of the tubular body part.

The pair of fixing balloons and the tube opening and closing balloon are configured in a manner such that they can be inflated and deflated through air passages defined in the tube. Further, a plurality of injection passages are defined in the tube so that an enema and an antibiotic solution for disinfecting an anastomosed portion of the intestinal tract can be injected through the injection passages.

The fecal discharging device constructed as mentioned above is fitted into the intestinal tract of the patient. Then, by supplying air into the pair of fixing balloons attached to the circumferential outer surface of the tubular body part which is formed at the upper end of the tube, the fixing balloons are inflated. Thereafter, by clamping the intestinal tract around the clamping portion of the tubular body part using a clamping band, the fecal discharging device is fixedly held in the intestinal tract. Thus, when it is necessary to restrain fecal discharge, air is supplied into the tube opening and closing balloon to inflate it, whereby the tubular body part is closed. When it is necessary to allow fecal discharge, air is exhausted from the tube opening and closing balloon to deflate it, whereby, as the tubular body part formed at the upper end of the tube is opened, feces can be discharged to the outside through the tube without coming into contact with the anastomosed portion of the intestinal tract.

The indwelling fecal diverting device according to the present invention can be fixed in a colostomy device which is separately installed in an anal region of a patient.

BRIEF DESCRIPTION OF THE DRAWINGS

The above objects, and other features and advantages of the present invention will become more apparent after a reading of the following detailed description when taken in conjunction with the drawings, in which.

BEST MODE FOR CARRYING OUT THE INVENTION

Figure 1:
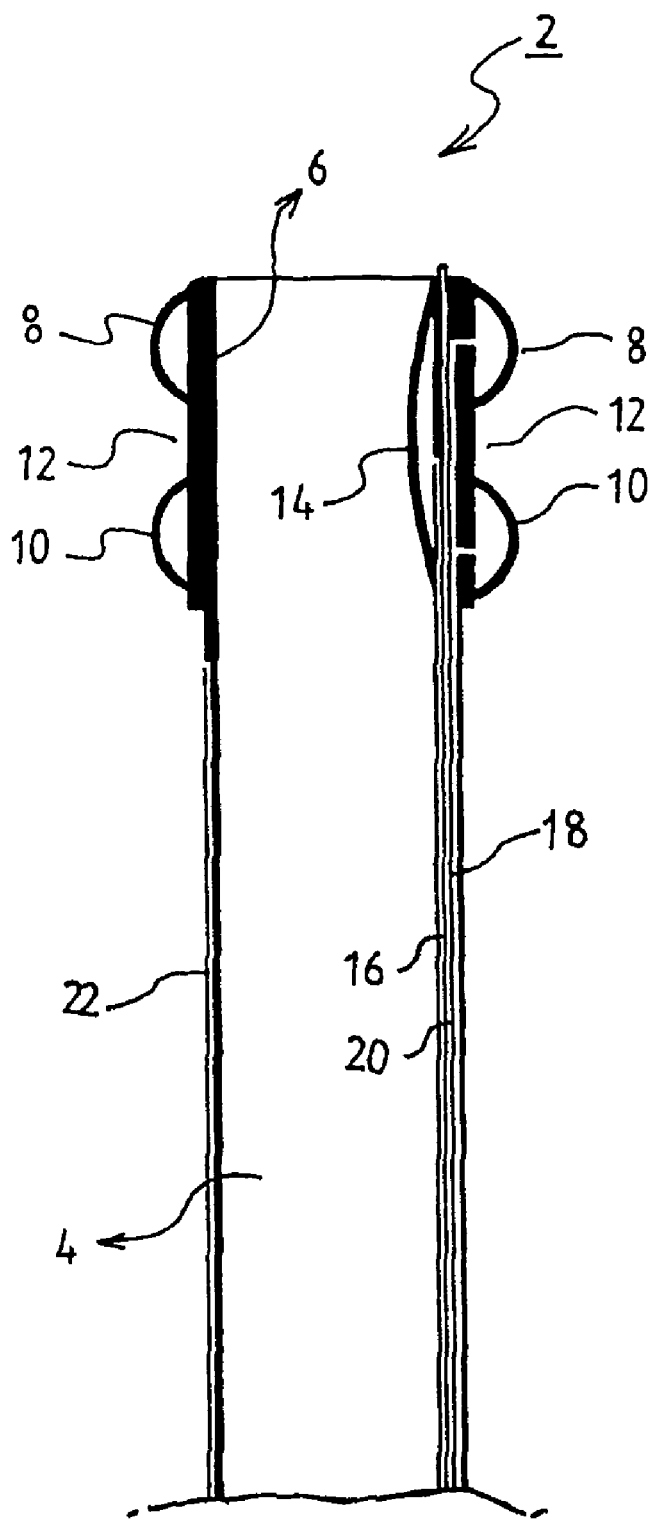
FIG. 1 is a cross-sectional view illustrating an indwelling fecal diverting device in accordance with an embodiment of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 is a cross-sectional view illustrating an indwelling fecal diverting device in accordance with an embodiment of the present invention. The indwelling fecal diverting device 2 comprises an elongate tube 4. The tube 4 is made of a material which is harmless to the human body and is capable of being freely flexed. A tubular body part 6 is formed at an upper end of the tube 4.

A pair of fixing balloons 8 and 10 are attached up and down to a circumferential outer surface of the tubular body part 6 in a manner such that a clamping portion 12 is defined between the fixing balloons 8 and 10. The thickness of the clamping portion is greater than the thickness of the tube. A tube opening and closing balloon 14 is attached to a circumferential inner surface of the tubular body part 6. The pair of fixing balloons 8 and 10 and the tube opening and closing balloon 14 are configured in a manner such that they can be inflated and deflated by air which is supplied into and discharged from them through air passages 16 and 18 defined in the tube 4.

In the indwelling fecal diverting device 2 according to the present invention, configurations in which air is supplied into and discharged from the fixing balloons 8 and 10 and the tube opening and closing balloon 14 to inflate and deflate them and a configuration of a first injection passage 20 for injecting an enema can be the same as those described in Korean Utility Model Publication No. 97-2898 entitled "Medical Colostomy Device" and filed in the name of the present applicant.

In brief, air is supplied into and discharges from the fixing balloons 8 and 10 and the tube opening and closing balloon 14 through the air passages 18 and 16, respectively. The injection passage 20 for injecting the enema is defined between the air passages 16 and 18. One-way valve means is provided at an upper end of the injection passage 20 to prevent backflow of the enema.

Figure 2:
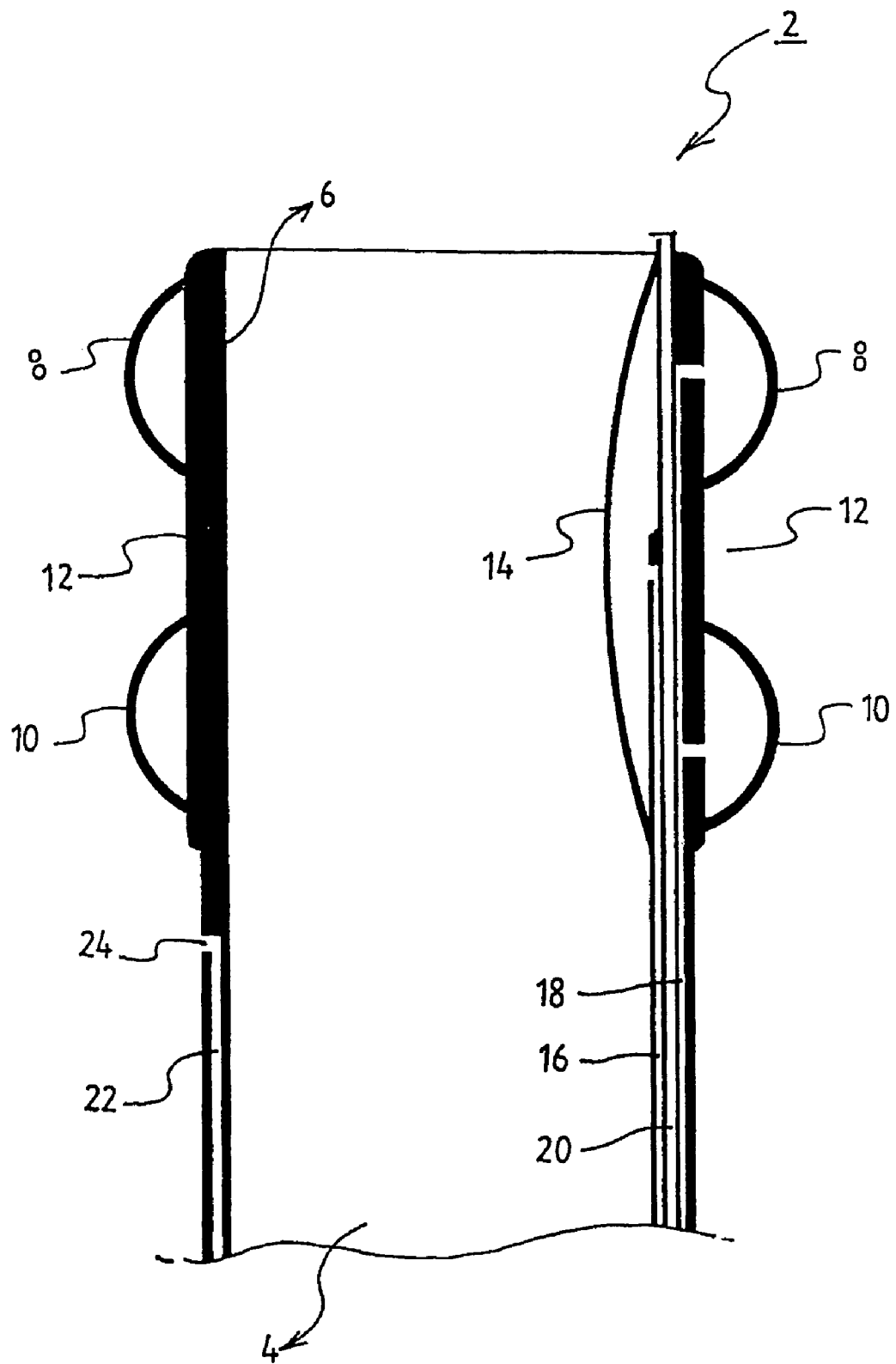
FIG. 2 is an enlarged view of FIG. 1.

A second injection passage 22 is defined in the tube 4 oppositely to the first injection passage 20. As shown in FIG. 2, an outlet 24 of the second injection passage 22 is opened to the outside of the tube 4 so that a remedial liquid such as an antibiotic solution, and the like, or a contrast medium for confirming safety of an anastomosed portion 30 can be injected into an intestinal tract of a patient (FIG. 3).

Figure 3:
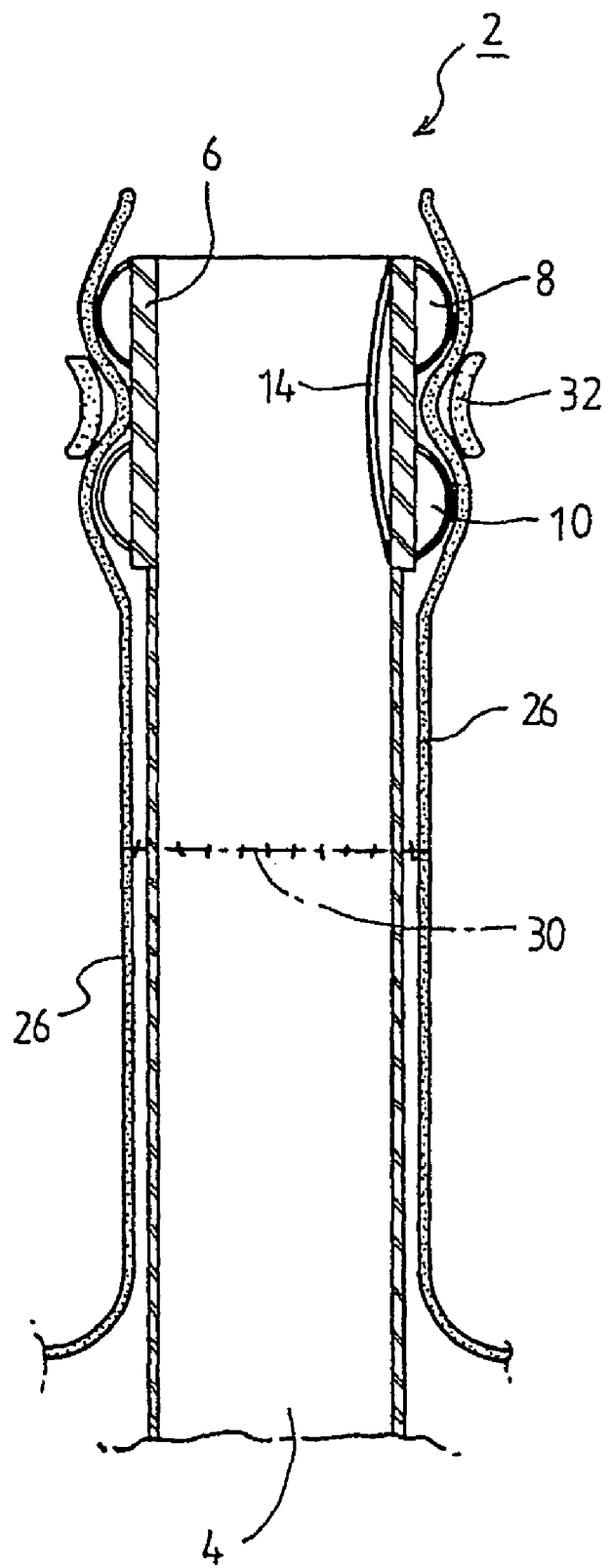
FIG. 3 is a cross-sectional view illustrating a state wherein the indwelling fecal diverting device according to the present invention is fixed in an intestinal tract.

The indwelling fecal diverting device 2 according to the present invention, constructed as mentioned above, is used when there is concern about leakage of liquid and gas at the anastomosed portion 30 of the intestinal tract after the patient has undergone an operation on a large intestine 26 or a rectum 28 (FIG. 3).

Figure 5:
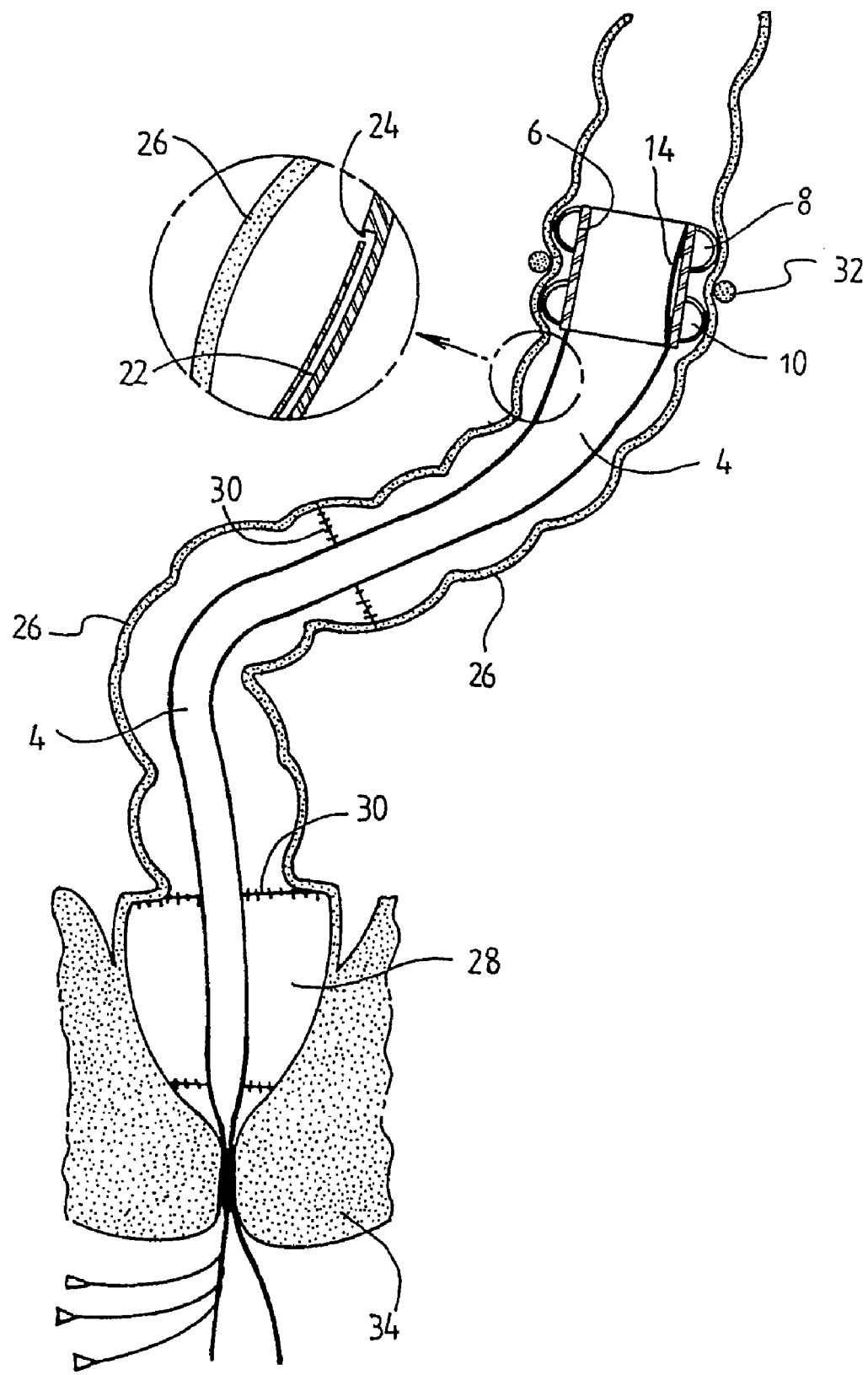
FIG. 5 is a partially enlarged cross-sectional view illustrating a state wherein the indwelling fecal diverting device according to the present invention is actually fixed in the intestinal tract.

That is to say, in a state wherein air is completely discharged from the fixing balloons 8 and 10 which are attached up and down to the circumferential outer surface of the tubular body part 6. As shown in FIG. 5, the indwelling fecal diverting device 2 is pushed into the large intestine 26 through the anus 34 of the patient so that the fixing balloons 8 and 10 attached to the tubular body part 6 are positioned upward of the anastomosed portion 30.

Then, as can be readily seen from FIG. 5, air is supplied into the fixing balloons 8 and 10 through the air passage 18 to inflate them. Then, by clamping the large intestine 26 around the clamping portion 12 of the tubular body part 6 using a clamping band 32 (FIGS. 4 and 4), the indwelling fecal discharging device 2 is fixedly held in the large intestine 26. At this time, the indwelling fecal discharging device 2 is prevented from being released from the large intestine 26 by virtue of the upper and lower fixing balloons 8 and 10 expanded on the circumferential outer surface of the tubular body part 6.

The clamping band 32 serving as means for fixing the indwelling fecal diverting device 2 in the large intestine 26 is loosely placed around the large intestine 26 so long as release of the inflated fixing balloons 8 and 10 from the large intestine 26 is prevented. The clamping band 32 is made of a material which can be absorbed into the human body and maintain its strength for about one month.

Figure 4:
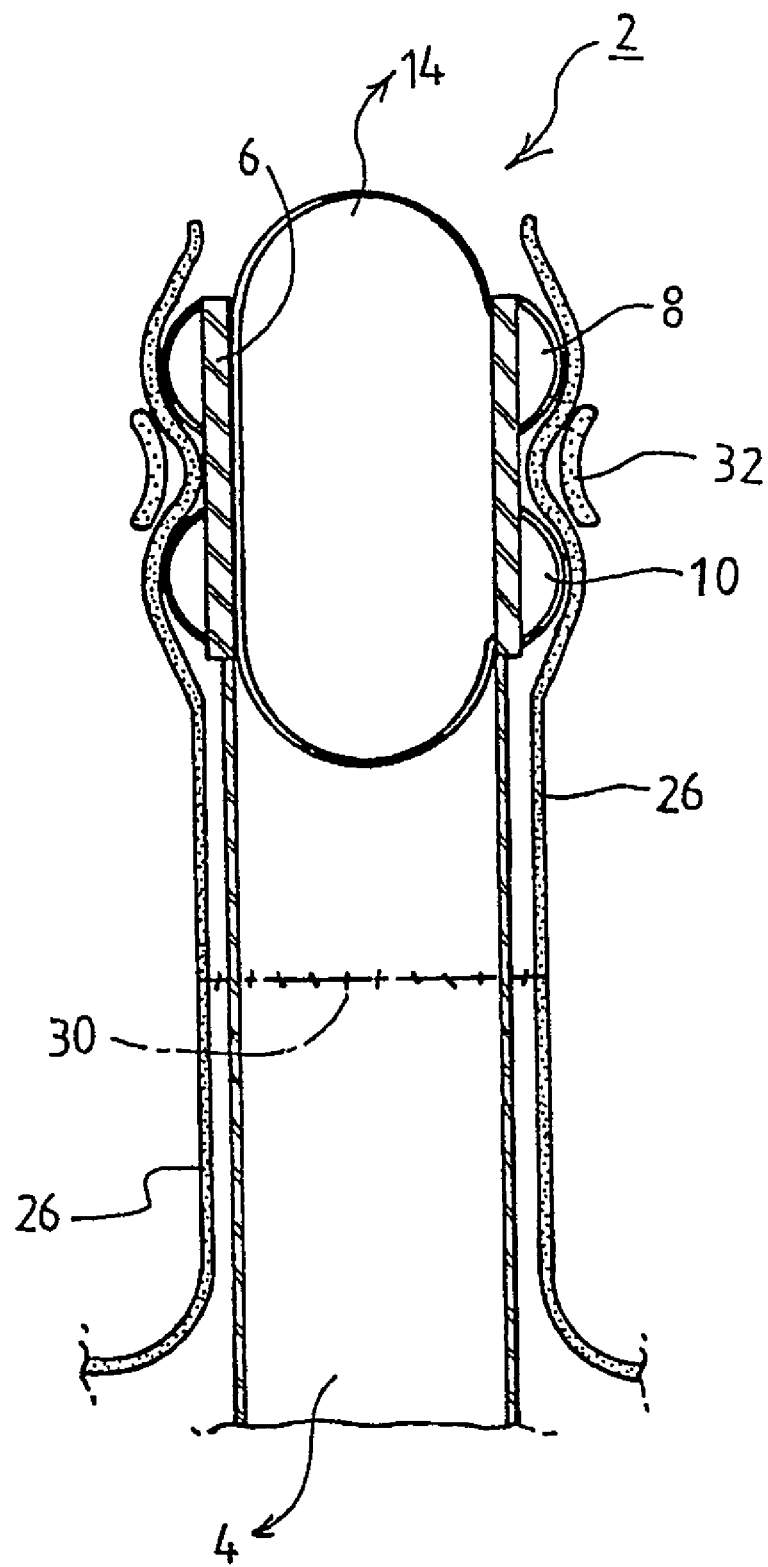
FIG. 4 is a cross-sectional view similar to FIG. 3, with a tube opening and closing balloon inflated.
Figure 6:
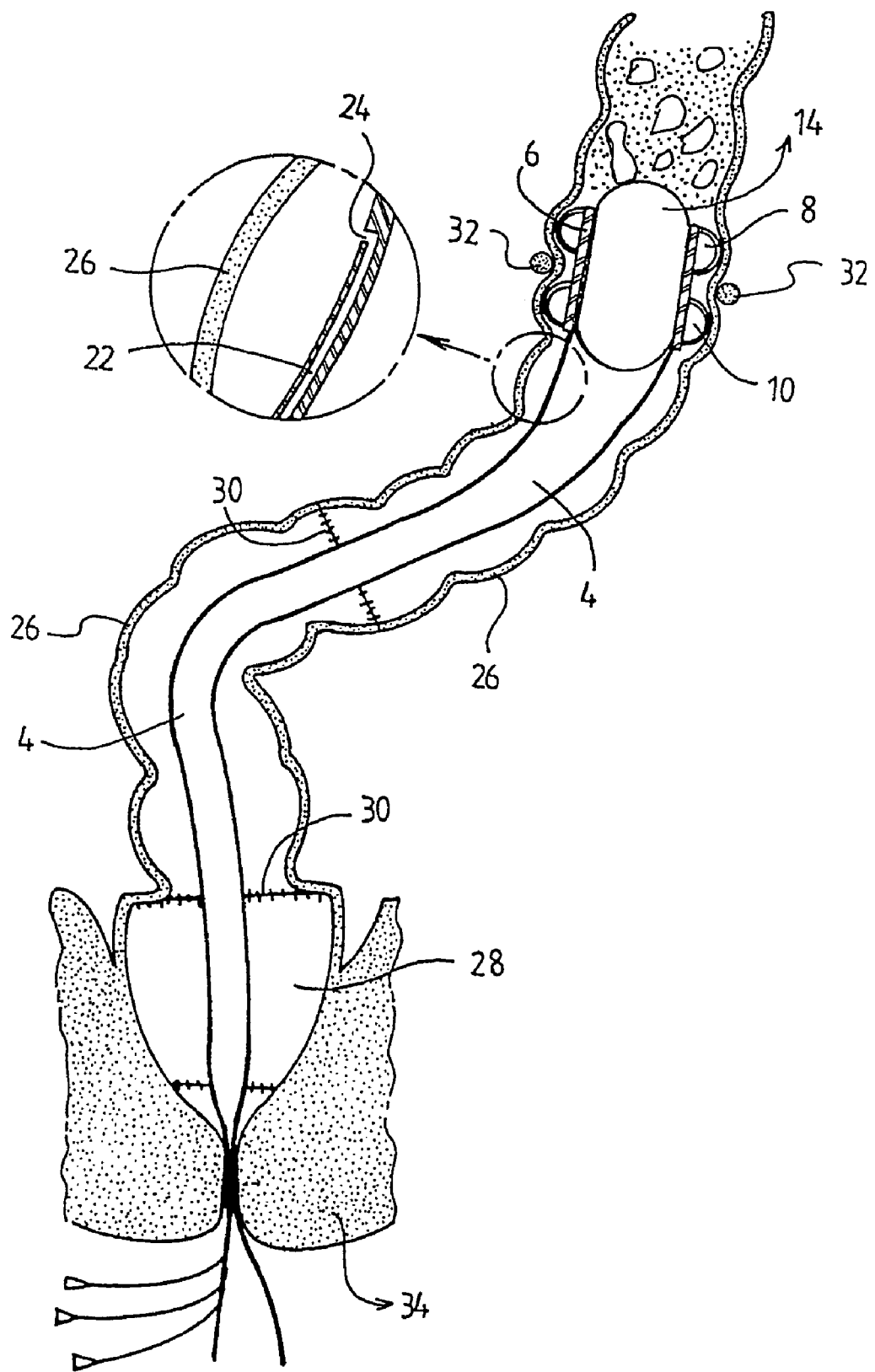
FIG. 6 is a partially enlarged cross-sectional view similar to FIG. 5, with the tube opening and closing balloon inflated.

In the above state, if air is supplied into the tube opening and closing balloon 14 through the air passage 16, as the tube opening and closing balloon 14 is inflated and the tubular body part 6 is closed as shown in FIGS. 4 and 6, feces are stagnated above the tubular body part 6.

When it is necessary to discharge the feces, as the air supplied into the tube opening and closing balloon 14 is exhausted, since the tubular body part 6 is opened as shown in FIG. 5, the feces are discharged through the tube 4. Therefore, since the feces can be discharged to the outside without coming into contact with the anastomosed portion 30 of the large intestine 26, the anastomosed portion 30 can be reliably protected.

As occasion demands, an enema, etc. can be injected through the first injection passage 20 to irrigate the intestinal tract and/or the tube 4. Also, a remedial liquid such as an antibiotic solution, and the like, can be injected through the second injection passage 22 into the intestinal tract of the patient, whereby the anastomosed portion 30, for example, of the large intestine 26, can be disinfected or medically treated.

While in use, if it is necessary to remove the indwelling fecal diverting device 2 from the large intestine 26, by exhausting air from the fixing balloons 8 and 10 which are attached to the circumferential outer surface of the tubular body part 6, the indwelling fecal diverting device 2 is freed from the clamping band 32. In this state, by pulling the tube 4, the indwelling fecal diverting device 2 can be easily removed from the large intestine 26. In this way, easy removal of the device 2 is guaranteed.

At this time, because the clamping band 32, which is placed around the large intestine 26, is absorbed into the human body with the lapse of time, no problem is caused.

A person skilled in the art will readily recognize that the indwelling fecal diverting device 2 according to the present invention can be fixed in a colostomy device which is separately installed in an anal region of a patient.

As apparent from the above description, the indwelling fecal diverting device according to the present invention provides advantages in that, since it is disposed upward of an anastomosed portion of an intestinal tract when there is concern about leakage of liquid and gas at the anastomosed portion of a rectum or large intestine after a patient has undergone an operation on the rectum or large intestine, feces can be discharged without coming into contact with the anastomosed portion, whereby the anastomosed portion is effectively protected, superior safety and easy installation thereof are ensured, and convenient use thereof is provided.

The invention claimed is:

1. An indwelling fecal diverting device comprising:
   an elongate tube;
   a tubular body part formed at an upper end of the elongate tube;
   at least a pair of fixing balloons attached to a circumferential outer surface of the tubular body part;
   a tube opening and closing balloon attached to a circumferential inner surface of the tubular body part;
   a first injection passage disposed within the tubular body part, the first injection passage spaced radially outwardly of the tube opening and closing balloon, an end of the first injection passage being above the pair of fixing balloons; and
   a second injection passage defined in the tube, the second injection passage terminating in a second outlet below the pair of fixing balloons and open to a circumferential outer surface of the elongated tube.

2. The device as set forth in claim 1, further comprising a liquid source connected to the second injection passage, wherein the liquid source is a remedial liquid that can be injected through the injection passage to the outside of the tube to medically treat an anastomosed portion of an intestinal tract of a patient.

3. The device as set forth in claim 1, wherein the indwelling fecal diverting device is fixedly held in the intestinal tract of the patient in a manner such that it is fitted into the intestinal tract of the patient, air is supplied into the pair of fixing balloons to inflate them, and the intestinal tract is clamped around a clamping portion of the tubular body part using a clamping band.

4. The device as set forth in claim 1, wherein the first injection passage is provided with a first outlet which is disposed at the top thereof and disposed between the pair of fixing balloons and the tube opening and closing balloon, and is opened to the outside of the elongated tube.

5. The device as set forth in claim 1, wherein the first injection passage is spaced radially inwardly of the pair of fixing balloons.

6. An indwelling fecal diverting device for the post-surgical protection of an intestinal anastomosis comprising:
   a flexible elongate tube;
   a tubular body formed at the upper end of the elongate tube;
   at least a pair of fixing balloons attached to a circumferential outer surface of the tubular body part; and
   the entire distance between the fixing balloons defining a clamping portion, the entire clamping portion having a thickness greater than a thickness of the tube.

7. The device as set forth in claim 6, further comprising a clamp between the pair of fixing balloons.

8. The device as set forth in claim 7, wherein the clamp is bioabsorbable.

9. The device as set forth in claim 6, further comprising:
   a tube opening and closing balloon attached to a circumferential inner surface of the tubular body part; and
   an injection passage with an outlet below the pair of fixing balloons and open to a circumferential outer surface of the elongated tube for the administration of remedial liquids for therapeutic or diagnostic purposes.

10. The device as set forth in claim 6, wherein the clamping portion has a substantially constant thickness.

11. An indwelling fecal diverting device comprising:
    an elongate tube;
    a tubular body part formed at an upper end of the elongate tube;
    a pair of fixing balloons attached to a circumferential outer surface of the tubular body part in a manner such that a clamping portion is defined between the fixing balloons;
    a tube opening and closing balloon attached to a circumferential inner surface of the tubular body part;
    a first injection passage disposed within the tubular body part, the first injection passage spaced radially outwardly of the tube opening and closing balloon, an end of the first injection passage being above the pair of fixing balloons;
    a second injection passage defined in the tube, the second injection passage provided with a second outlet below the pair of fixing balloons and open to a circumferential outer surface of the elongated tube; and
    a clamp fitting around the tubular body part at the clamping portion.

12. The device as set forth in claim 11, wherein the clamp is between the fixing balloons.

13. The device as set forth in claim 11, wherein the clamp is bioabsorbable.

* * * * *